United States Patent [19]

Bieniarz et al.

[11] Patent Number: 4,994,385

[45] Date of Patent: Feb. 19, 1991

[54] HETEROBIFUNCTIONAL COUPLING AGENTS

[75] Inventors: Christopher Bieniarz, Highland Park; Christopher J. Welch, Urbana; Grady Barnes, Lindenhurst, all of Ill.

[73] Assignee: Abbott Laboratories, Abbott Park, Ill.

[21] Appl. No.: 246,971

[22] Filed: Sep. 22, 1988

Related U.S. Application Data

[63] Continuation-in-part of Ser. No. 114,930, Oct. 30, 1987, abandoned.

[51] Int. Cl.$^5$ .................. C12N 11/14; C07K 17/06
[52] U.S. Cl. .................. 435/177; 435/188; 435/174; 435/7.9; 435/21; 435/28; 435/7.92; 435/964; 436/547; 530/391; 530/389; 530/388; 530/390; 525/54.1
[58] Field of Search .............. 548/520, 546; 530/390, 530/391; 435/188, 174, 177, 181, 7, 21, 28; 424/85, 91; 525/54.1; 436/547

[56] References Cited

U.S. PATENT DOCUMENTS

| | | | |
|---|---|---|---|
| 4,278,651 | 7/1981 | Hales | 436/532 |
| 4,302,386 | 11/1981 | Stevens | 530/322 |
| 4,582,789 | 4/1986 | Sheldon, III et al. | 435/6 |
| 4,695,624 | 9/1987 | Marburg | 530/395 |
| 4,794,082 | 12/1988 | Sigler | 435/177 |

FOREIGN PATENT DOCUMENTS

| | | | |
|---|---|---|---|
| 0109653 | 5/1984 | European Pat. Off. | 435/174 |
| 62-83665 | 4/1987 | Japan . | |
| WO88/03412 | 5/1988 | PCT Int'l Appl. . | |

OTHER PUBLICATIONS

Keller, O. and Rudinger, J. (1975) "Preparation and Some Properties of Maleimido Acids and Maleoyl Derivatives of Peptides" Helvetica Chemica Acta 58(FASC2 Nr. 63); 531–541.
Yoshitake, S. et al. (1982) J. Biochem. 92:1413–1424.
The Clontech "Spring 1987 Product Guide".
The Clonentech "Spring 1987 Product Update".
Fischer, et al., *Acta. Biol. Med. Germ.*, Band 36, pp. 999–1005 (1972).
Freytag, et al., *Clinical Chemistry*, 30(9):1494–1498 (1984).
Imagawa, et al., *Journal of Applied Biochemistry*, 4:41–57 (1982).
Kato, et al., *Rinsho Kagaku Shimpojumu*, No. 16, pp. 10–14 (1976).
Kato, et al., *Igaku No Ayumi*, 104(12):805–807 (1978).
Kitagawa, et al., *Chem. Pharm. Bull.*, 29(4):1130–1135 (1981).
Manecke, et al., *Biochimie*, 62:603–613 (1980).
Yoshitake, et al., *Analytical Letters*, 15(B2):147–160 (1982).
Yoshitake, et al., *Europ. J. Biochem*, 101:395–399 (1979).

*Primary Examiner*—Howard E. Schain
*Assistant Examiner*—Kay Kim
*Attorney, Agent, or Firm*—Thomas M. Breininger; Daniel W. Collins; Robert W. Stevenson

[57] ABSTRACT

Novel polyamino acid based coupling agents are disclosed. These reagents are useful for conjugating proteins (e.g. antibodies to enzymes) for use in diagnostic assays.

16 Claims, No Drawings

HETEROBIFUNCTIONAL COUPLING AGENTS

BACKGROUND OF THE INVENTION

This application is a continuation-in-part of U.S. application Ser. No. 114,930 filed Oct. 30, 1987, now abandoned.

The present invention relates to couplinq agents for covalent conjugation of proteins for use in diagnostic assays.

It is well established that a protein such as an enzyme can be conjugated via a linker group to another protein such as an antibody to form a conjuqate which can be used in enzyme immunoassays (EIAs).

In the past, conjuqates have been formed usinq heterobifunctional reagents which are quite short in comparison with the protein molecules being conjugated. It is believed that by restricting the conformational freedom of a protein, the function of the protein (e.g., initial rate, turnover number, and Km for an enzyme, or $K_{aff}$ for an antibody) can be adversely affected, thereby rendering the individual components of an enzyme-antibody conjugate less active than their unconjugated counterparts. This has been a problem which has limited the bioactivity of enzyme-antibody conjugates and their application to immunoassays.

SUMMARY OF THE INVENTION

The present invention is a heterobifunctional coupling agent of formula I:

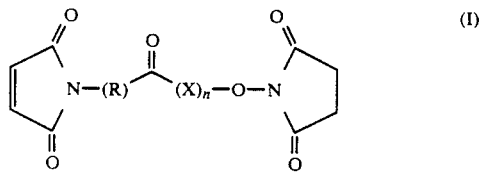

wherein X is a substituted or unsubstituted amino acid having from three to ten carbon atoms in a straight chain.

R is an alkyl, cycloalkyl, an alkyl-cycloalkyl, or an aromatic carbocyclic ring; and n is from one to ten.

Other aspects of the invention include conjugates of proteins, or of proteins and small molecules such as haptens made with the coupling agent described above.

It was discovered that utilizing a long, hydrophylic chain between the two reactive ends of the coupling agent described above yields a coupling agent which produces conjugates which often retain more of the native activity and stability of the conjugated proteins than conjugates made using previously existing methods.

The present invention also includes conjugates of formula II:

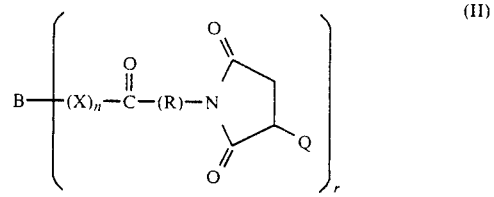

wherein X, n, and R are as defined above; B is an antibody or enzyme; Q is an antibody when B is an enzyme, and an enzyme when B is an antibody; and r is from one to fifty. With this conjugate, many enzyme markers can be attached to a single antibody (or vice versa) to get a large response in an immunoassay.

The present invention also includes immunogens of formula II where X, n, and R are as defined above, B is a polyaminoacid, and Q is a hapten.

DETAILED DESCRIPTION OF THE INVENTION

The coupling agent of formula I can be used to conjugate enzymes to antibodies, haptens to hapten carriers, or virtually any protein to another protein. Using a coupling agent of formula I in such conjugates produces a conjugate where the normal activity of the antibody, enzyme or protein is retained. It is believed that prior coupling agents, by virtue of their short overall length in comparison with the size of the proteins being conjugated produce conjugates in which the conformational freedom of the individual proteins is compromised. This loss of conformational freedom can lead to diminished activity of either or both proteins in the conjugate resulting in poorer performance in EIAs or poorer stability of the reagent. Thus, many prior coupling agents have limited usefulness.

The long hydrophylic chain of amino acids in the coupling agents of the present invention not only provide better physical separation of the conjugated proteins, but also are solvated well by water in the solution, in contrast to often used hydrophobic spacer groups in previous coupling reagents. The coupling agents of this invention are thus well suited for use in aqueous solutions.

The following examples illustrate the synthesis and uses of conjugates of the present invention. The designation R, X and n have the meanings previously assigned. The term "alkyl-cycloaklyl" as used herein for "R" includes alkyl groups linked to cycloalkyl ring structures where the alkyl group links the cycloalkyl to the maleimide or the carbonyl groups. The term "alkyl" includes straight or branched alkyl groups, preferably lower groups having from one to six carbon atoms.

EXAMPLE 1

Synthesis of:

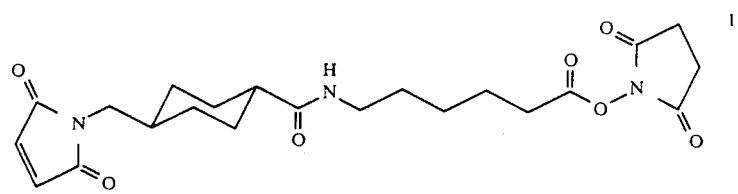

Trans-4-(aminomethyl) cyclohexanecarboxylic acid (Aldrich Chemical Co.) is converted to N-(4-carboxycyclohexylmethyl) maleimide by the method of Yoshitake et al. (*J. Biochem.*, 101:395–399 (1979)). This material (100 mg) is then dissolved in dry dimethylformamide (DMF) (1.0 ml), 6-aminocaproic acid (39.23 mg; 1.0 eq) is added, and the resulting mixture is stirred overnight at room temperature under nitrogen atmosphere. The following morning, dicyclohexylcarbodiimide (DCCI) (67.8 mg; 1.1 eq) and N-hydroxysuccinimide (37.8 mg; 21 eq) are added, and the reaction mixture is stirred for an additional six hours. Precipitated dicyclohexylurea (DCU) is removed by filtration, and the resulting DMF solution is evaporated under reduced pressure to give a tacky solid, which is purified by flash chromatography upon silica gel (5% methanol/chloroform) to give compound 1 (71 mg) as a white solid in 53% overall yield. (Formula I; R=cyclohexylmethyl; n=1; X=6-aminocaproyl).

EXAMPLE 2

Synthesis of:

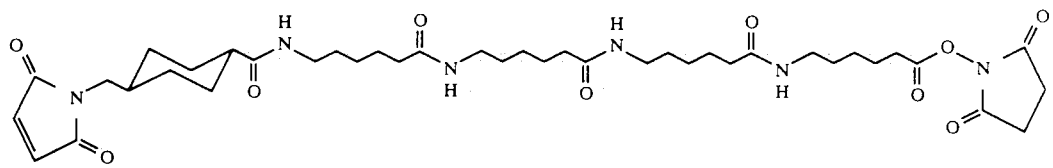

Compound 1 (100 mg; synthesis described in Example 1) is dissolved in dry DMF (1.0 ml), 6 aminocaproic acid (29.3 mg; 1.0 eq) is then added, and the resulting mixture is stirred overnight at room temperature under nitrogen atmosphere. The following morning, DCCI (50.7 mg; 1.1 eq) is added, and the reaction mixture is stirred for an additional six hours. Solid precipitate (DCU) is removed by filtration, and the resulting DMF solution is evaporated under reduced pressure to give a tacky solid, which is purified by flash chromatography upon silica gel (10% methanol/chloroform) to give compound 2 (60 mg) as a white solid in 48% overall yield. (Formula I; R=cyclohexylmethyl; n=2; X=6-aminocaproyl).

EXAMPLE 3

Synthesis of:

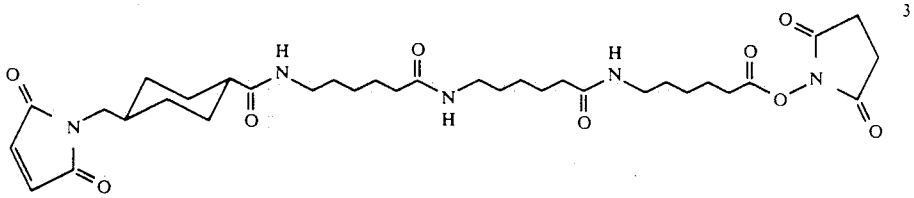

Compound 2 (100 mg; synthesis described in Example 2) is dissolved in dry DMF (2.0 ml), 6-aminocaproic acid (23.4 mg; 1.0 eq) is then added and the resulting mixture is stirred overnight at room temperature under nitrogen atmosphere. The following morning, DCCI (40.5 mg; 1.1 eq) is added, and the reaction mixture is stirred for an additional six hours. Solid precipitate (DCU) is removed by filtration, and the resulting DMF solution is evaporated under reduced pressure to give a tacky solid, which is purified by flash chromatoqraphy upon silica gel (10% methanol/chloroform) to give compound 3 (60.0 mg) as a white solid in 50% overall yield. (Formula I; R=cyclohexylmethyl; n=3; X=6-aminocaproyl).

EXAMPLE 4

Synthesis of:

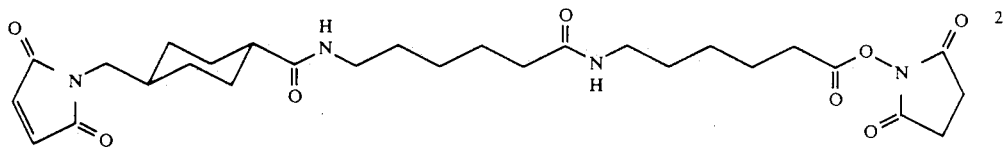

Compound 3 (100 mg; synthesis described in Example 3) is dissolved in dry DMF (10.0 ml), 6-aminocaproic acid (19.5 mg; 1.0 eq) is then added, and the resulting mixture is stirred overnight at room temperature under nitrogen atmosphere. The following morning DCCI (33.7 mg; 1.1 eq) is added, and the reaction mixture is stirred for an additional six hours. Solid precipitate (DCU) is removed by filtration, and the resulting DMF solution is evaporated under reduced pressure to give a tacky solid, which is purified by flash chromatography upon silica gel (10% methanol/chloroform) to give compound 4 (53 mg) as a white solid in 45% overall yield. (Formula I, R=cyclohexylmethyl; n=4; X=6-aminocaproyl).

EXAMPLE 5

Conjugation of Monoclonal Anti-Alpha Fetoprotein IgG With Calf Intestinal Alkaline Phosphatase Using Compound 3

(a) Derivatization of Enzyme

A solution of calf intestinal alkaline phosphatase (250 ul; 10 mg/ml; Boehrinqer-Mannheim) is placed in a vial. A solution of compound 3 in DMF (100 ul; 5.0 mM) is added, and the resulting mixture is stirred on a rotary agitator for thirty minutes at room temperature. The crude reaction mixture is purified by chromatography upon a pre-equilibria Sephadex G-25 (coarse) column with pH 7.0 phosphate buffer (0.1M phosphate, 0.1 M NaCl, 1 mM $MgCl_2$, 0.1 mM $ZnCl_2$) as eluent.

Fractions from the column are collected, enzyme containing fractions are pooled, and protein concentration of the pooled fractions is estimated by measuring absorbance at 280 nm. In our hands the absorbance at 280 nm was found to be approximately equal to protein concentration in mg/ml.

(b) Antibody Derivatization

Monoclonal anti AFP IgG solution at 6.4 mg/ml is incubated at room temperature with DTT (dithiothreotol; 25 mM concentration in the final reaction solution) for twenty minutes with stirring on a rotary agitator. The solution of partially reduced antibody is then purified by chromatography upon a pre-equilibria Sephadex G-25 (coarse) column with pH 7.0 phosphate buffer (0.1M phosphate, 0.1M NaCl, 5 mM ERDTA) as eluent.

Fractions from the column are collected, protein containing fractions are pooled, and protein concentration of the pooled solution is estimated by measuring absorbance at 280 nm. In this instance absorbance at 280 nm divided by a factor of 1.39 is approximately equal to antibody concentration in mg/ml.

(c) Conjugation of Partially Reduced Antibody With Derivatized Alkaline Phosphatase The derivatized alkaline phosphatase from Part (a) is combined with the partially reduced antibody from. Part (b) in a molar ratio of 1.5:1 enzyme to antibody. The mixture is stirred overnight at 2°–8° C. on a rotary agitator. The following morning, unreacted thiol groups are capped by treatment with an N-ethylmaleimide (NEM) solution (100 ul; 5.0 mM) for a period of one hour at room temperature. The conjugate concentrate thus obtained can be diluted as necessary for use in a sandwich assay or any other assay where a labeled antibody is to be used. (Formula II; B=calf intestinal alkaline phosphatase; R=cyclohexylmethyl; X=6-aminocaproyl; n=3; Q=monoclonal anti-AFP IgG; and r is from one to five).

EXAMPLE 6

Conjugation of β-Galactosidase to Goat Anti-Rabbit IgG Using Compounds 1, 2, or 3

(a) Antibody Derivatization with Compound 1

Goat anti-rabbit IgG (1.0 mg) is suspended with pH 7.0 phosphate buffer (1.0 ml; 15 mM phosphate; 150 mM NaCl; 1.0 mM EDTA). An aliquot of this solution (425 ul) is then added to a solution of compound 1 in DMF (12.75 ul; 6.0 mM). The mixture is incubated in the dark for sixty minutes at room temperature with occasional mixing. The crude reaction mixture is then dialyzed overnight in the dark at 4° C. against pH 7.0 phosphate buffer (2.0 l; 15 mM phosphate; 150 mM NaCl; 1 mM EDTA). The dialyzed material is recovered by centrifugation, and antibody concentration is estimated by measuring absorbance at 280 nm. In our hands $A_{280}$ divided by a factor of 1.38 is approximately equal to antibody concentration in mg/ml.

(b) Conjugation of Derivatized Antbibody With Native β-Galactosidase

The derivatized antibody from Part a) and native *E. coli* β-galactosidase (25 mg/ml in pH 7.0 phosphate buffer) are combined in a molar ratio of 0.6:1 enzyme to antibody. The mixture is allowed to react overnight at room temperature without stirring to yield a concentrated solution of conjugate for use in an immunoassay. (Formula II; B=goat anti rabbit IgG; R=cyclohexylmethyl; X=6 aminocaproyl; n=1; Q=β-Galactosidase and r=from one to five).

(c) Antibody Derivation with Compound 2

Goat anti-rabbit IgG (1.0 mg) is suspended with pH 7.0 phosphate buffer (1.0 ml; 15 mM phosphate; 150 mM NaCl; 1.0 mM EDTA). An aliquot of this solution (425 ul) is then added to a solution of compound 2 in DMF (12.75 ul; 6.0 mM). The mixture is incubated in the dark for sixty minutes at room temperature with occasional mixing. The crude reaction mixture is then dialyzed overnight in the dark at 4° C. against pH 7.0 phosphate buffer (2.0 L; 15 mM phosphate; 150 mM NaCl; 1 mM EDTA). The dialyzed material is recovered by centrifugation, and antibody concentration is estimated by measuring absorbance at 280 nm. In our hands $A_{280}$ divided by a factor of 1.38 is approximately equal to antibody concentration in mg/ml.

Antibody derivatized with compound 2 can be coupled to native β-Galactosidase as described in Part (b) above. (Formula II; B=goat anti-rabbit IgG; R=cyclohexylmethyl; X=6-aminocaproyl; n=2; Q=β-Galactosidase and r=from one to five).

(D) Antibody Derivatization with Compound 3

Goat anti rabbit IgG (1.0 mg) is supended in pH 7.0 phosphate buffer (1.0 ml; 15 mM phosphate; 150 mM NaCl; 1.0 mM EDTA). An aliquot of this solution (425 ul) is then added to a solution of compound 3 in DMF (12.75 ul; 6.0 mM). The mixture is incubated in the dark for sixty minutes at room temperature with occasional mixing. The crude reaction mixture is then dialyzed overnight in the dark at 4° C. against pH 7.0 phosphate buffer (2.0 L; 15 mM phosphate; 150 mM NaCl; 1 mM EDTA). The dialyzed material is recovered by centrifugation, and antibody concentration is estimated by measuring absorbance at 280 nm. In our hands $A_{280}$ divided by a factor of 1.38 is approximately equal to antibody concentration in mg/ml.

Antibody derivatized with compound 3 can be coupled to native β-galactosidase as described in Part (b) above. (Formula II; B=goat anti-rabbit IgG; R=cyclohexylmethyl; X=6-aminocaproyl; n=3; Q=β-galactosidase and r=from one to five).

EXAMPLE 7

Preparation of Polyclonal anti-TSH (Thyroid Stimulating Hormone)-Alkaline Phosphatase Conjugate Using Compound 1

(a) Derivatization of the Enzyme

Calf intestinal alkaline phosphatase (25 ul; 10 mg/ml) is combined with a solution of compound 1 in DMF (10 ul; 7.8 mM) and allowed to react for thirty minutes at room temperature. The crude reaction mixture is purified by passage through a mini-gel filtration (G-25 Sephadex) column while centrifuging, the column being equilibria with 0.05M phosphate buffer at pH 7.0. A purified solution of a linker derivatized enzyme is obtained.

(b) Antibody Derivatization

A polyclonal anti-TSH IgG solution (25 ul; 5.3 mg/ml) is mixed with a solution of DTT (25 ul; 0.1M) in pH 7.0 phosphate buffer (0.5M phosphate). The mixture is allowed to react for thirty minutes at room temperature, then purified in the same manner as the derivatized enzyme in Part (a).

(c) Conjugation of Enzyme and Antibody

The products of Part (a) and Part (b) are combined, incubated overnight at 2°-8° C., and a conjugate of anti-TSH with alkaline phosphatase is obtained. This conjugate can be used in sandwich assays for TSH. (Formula II; B=alkaline phosphatase; R=cyclohexylmethyl; X=6-aminocaproyl; n=1; Q=polyclonal anti-TSHG IgG; and r=from one to five).

EXAMPLE 8

Conjugation of Horseradish Peroxidase to Fab' Anti-Hepatitis B Core Antibody Using Compound 3

(a) Derivatization of the Enzyme

A horseradish peroxidase solution (400 ul; 10 mg/ml) in pH 7.0 phosphate buffer (0.1M phosphate; 0.1 M NaCl) is added to a solution of compound 3 (3.3 mg) in DMF (236 ul). The mixture is stirred for 30 minutes at room temperature, then desalted on a Sephadex G-25 (coarse) column using the above described buffer. Fractions are collected, enzyme containing fractions pooled, and concentration of pooled enzyme is estimated by measuring absorbance at 280 nm. In our hands $A_{280}$ divided by a factor of 0.61 is approximately equal to enzyme concentration in mg/ml.

(b) Derivatization of the Antibody

A solution of Fab' anti-hepatitis B core IgG fragment (3.1 ml; 3.2 mg/ml) is placed in a vial. Phosphate buffer (pH 7.0; 0.5M phosphate; 0.5M NaCl; 25 mM EDTA) is added. DTT (23.1 mg) is then added, and the mixture is incubated at room temperature for twenty minutes while stirring.

The crude product is then placed on a G-25 Sephadex column (coarse) and eluted with the above described pH 7.0 phosphate buffer.

Fractions are collected, protein containing fractions are pooled, and concentration of the pool is estimated by measuring absorbance at 280 nm. In our hands $A_{280}$ divided by a factor of 1.38 is approximately equal to antibody fragment concentration in mg/ml.

(c) Conjugation of Derivatized Alkaline Phosphatase With Antibody Fragment

Derivatized enzyme from Part (a) is combined with antibody fragment from Part (b) in a 1:1 enzyme to antibody ratio. The mixture is incubated overnight on a rotary agitator at 2°-8° C. The following morning the crude conjugate mixture is passed over a Con A-sepharose column. Unconjugated antibody fragments are washed away, and then conjugate is eluted with a 0.1M alpha-methyl glucoside solution. Recovered conjugate is dialyzed against buffer, diluted, and use in a sandwich assay for hepatitis B viral particles. (Formula II; B=alkaline phosphatase; R=cyclohexylmethyl; X=6-aminocaproyl; n=3; Q=Fab' anti-hepatitis B core antibody; and r is from one to five).

EXAMPLE 9

Conjugation of Calf Intestinal Alkaline Phosphatase to Bovine Gamma Globulin Specific for *E. Coli* Cell Wall Antigens Using Compound 2

(a) Enzyme Derivatization with Iminothiolane

To a solution of calf intestinal alkaline phosphatase (2.0 ml; 12.3 mg/ml) in pH 8.0 tris buffer (0.05 M triethanolamine (tris); 10 mM $MgCl_2$; 0.1 mM $ZnCl_2$) is added iminothiolane HCl such that final iminothiolane concentration in the reaction mixture is 4.0 mM.

The reaction mixture is stirred for one hour at 4° C. Excess glycinamide is then added to quench unreacted iminothiolane.

The crude reaction mixture is placed on a TSK 40 column and eluted with the pH 8.0 tris buffer described above.

Column fractions are collected, enzyme containing fractions are pooled, and protein concentration of the pool is estimated by measuring absorbance at 280 nm. In our hands $A_{280}$ divided by a factor of 0.76 is approximately equal to enzyme concentration in mg/ml.

(b) Antibody Derivatization with Compound 2

A solution of bovine gamma globulin (2.0 ml; 8.4 mg/ml; raised against cell wall antigens of *E. Coli*) in pH 8.0 tris buffer (0.5M tris; 0.16M NaCl; 1.0 mM $MgCl_2$; 0.1 mM $ZnCl_2$) is treated with a solution of compound 2 (3.36 mg) dissolved in DMF (859 ul) and incubated for one hour at 4° C. while stirring.

The crude reaction mixture is then placed on a TSK 40 column and eluted with the pH 8.0 tris buffer described above.

Column fractions are collected, protein containing fractions are pooled, and protein concentration of the pool is estimated by measuring absorbance at 280 nm. In our hands $A_{280}$ divided by a factor of 1.40 is approximately equal to enzyme concentration in mg/ml.

(c) Conjugation of Enzyme and Antibody

Derivatized enzyme from Part (a) is combined with derivatized antibody from Part (b) in a 1.1:1 (enzyme:antibody) ratio, and stirred at 4° C. overnight.

The following morning, the crude reaction mixture is added to an equal volume of pH 8.0 tris buffer (0.05 M tris; 1.0 mM $MgCl_2$; 0.1 mM $ZnCl_2$; 0.16M NaCl; 2% bovine serum albumin (BSA); 0.2% sodium azide). β-mercaptoethanol (10 ul) is then added, and the crude conjugate concentrate is stored in this form until needed. A 1:1000 dilution of this conjugate concentrate with an appropriate diluent gives about a 0.5 ug/ml solution of conjugate which can be used in a sandwich-type assay for various microorganisms. (Formula II; B=bovine gamma globulin; R=cyclohexylmethyl; X=6-aminocaproyl; n=2; Q=calf intestinal alkaline phosphatase; and r is from one to five).

EXAMPLE 11

Synthesis of Extended Length MBS Linkers (a) Synthesis of:

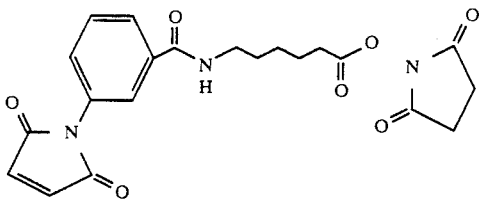

A 0.15M solution of m maleimidobenzoyl N-hydroxysuccinimide ester (MBS) (prepared according to the procedure of Kitagawa, et al., *J. Biochem.*, 79:233–236 (1976)) in dry DMF is treated with one equivalent of 6-aminocaproic acid and allowed to stir at room temperature overnight under nitrogen atmosphere. The following morning, 1.0 equivalent of dicyclohexylcarbodiimide (DCCI) is added, and the reaction mixture is stirred for an additional six hours at room temperature. Precipitated dicyclohexylurea (DCU) is then removed by filtration, and DMF is evaporated under high vacuum to give a crude product 5 which is purified by flash chromatography upon a silica gel column. (Formula I; R=a 3,5-disubstituted benzene ring; n=1; X=6-aminocaproyl).

(b) General Procedure for Synthesis of Extended Length Active Esters

To synthesize even longer linker arms based on MBS, or any active ester, a DMF solution of a compound containing a N hydroxysuccinimidyl ester (e.g., compound 5 from Part (a) is treated with 1.0 equivalent of 6-aminocaproic acid and allowed to stir at room temperature under nitrogen atmosphere until no more active ester is visible by TLC. 1.1 equivalent DCCI is then added, and the reaction mixture is stirred until N-hydroxysuccinimide is no longer visible by TLC. Precipitated DCU is then removed by filtration, DMF is evaporated under reduced atmosphere to yield a crude residue which is purified by flash chromatography on silica.

This procedure inserts a 6-aminocaproic acid residue into an active ester, and re-synthesizes the active ester. This insertion procedure can be repeated to yield a reagent of desired length, using 6-aminocaproic acid, or other amino acids.

EXAMPLE 12

Synthesis of Extended Length MCS Reagents (a) Synthesis of:

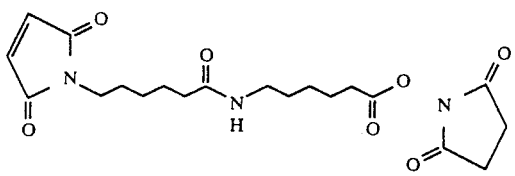

A 0.15M solution of 6-maleimidocaproic acid N-hydroxysuccinimide ester (MCS) (prepared according to the procedure described by Keller and Rudinger; *Helv. Chim Acta*, 58:531–541 (1975)) in dry DMF is treated with one equivalent of 6-aminocaproic acid, and allowed to stir overnight at room temperature under a nitrogen atmosphere. The following morning, 1.1 equivalent DCCI is added, and the reaction mixture is stirred for an additional six hours. Precipitated DCU is then removed by filtration, DMF is evaporated under high vacuum to give a crude product 6 which is purified by flash chromatography on silica. Longer analogs of 6 can be made by following the general homologation sequence described in Example 10, Part b. (Formula I; R=a 1,5-disubstituted pentyl group, n=1; X=6-aminocaproyl).

EXAMPLE 13

Conjugation of Monoclonal anti-Carcinoembryonic Antigen (CEA) IgG to Calf Intestinal Alkaline Phosphatase Using Compound 3

(a) Enzyme Derivatization

A solution of calf intestinal alkaline phosphatase (500 ul; 10.7 mg/ml) is mixed with a solution of compound 3 in dry DMF (200 ul; 5.0 mM) and stirred at room temperature for 30 minutes. The crude reaction mixture is then placed on a pre-equillibrated Sephadex G-25 column, and eluted with pH 7.0 phosphate buffer (0.1M phosphate; 0.1M NaCl 1 mM $MgCl_2$; 0.1 mM $ZnCl_2$).

Fractions from the column are collected, enzyme containing fractions are pooled, and enzyme concentration of the pooled fractions is estimated by measuring absorbance at 280 nm. In our hands the absorbance at 280 nm was found to be approximately equal to protein concentration in mg/ml.

(b) Antibody Derivatization

A solution of monoclonal anti CEA IgG at (315 ul; 9.5 mg/ml) is treated with 500 molar equivalents of a solution of iminothiolane hydrochloride in pH 8.0 phosphate buffer (0.033 mf/ml iminothiolane; 0.1M phosphate; 0.1 M NaCl; 5 mM EDTA). The reaction mixture is stirred at room temperature for 30 minutes, then placed on a pre-equillibrated Sephadex G-25 column, and eluted with the pH 8.0 phosphate buffer described above.

Fractions from the column are collected, antibody containing fractions are pooled, and protein concentration of the antibody pool is estimated by measuring absorbance at 280 nm. In our hands $A_{280}$ divided by a factor of 1.39 is approximately equal to antibody concentration in mg/ml.

(c) Conjugation of Enzyme and Antibody

Derivatized enzyme from Part (a) and derivatized antibody from Part (b) are combined in a 1:1 molar ratio, and allowed to stir overnight at 2°–8° C. The following morning, the conjugate is diluted to approximately 1 ug/ml concentration with an appropriate diluent, and used directly in a sandwich-type assay for carcinoembryonic antigen (CEA). (Formula 2; B=calf intestinal alkaline phosphatase; R=cyclohexylmethyl; X=6-aminocaproyl; n=3; Q=monoclonal anti CEA IgG; and r is from one to five).

EXAMPLE 14

Synthesis of Immunoqen (a) Functionalization of BSA with Compound 1

BSA (50.0 mg) is dissolved in 5.0 ml pH 6.6 phosphate buffer (0.1M phosphate). To this solution is added a solution of compound 1 (5.0 mg) in DMF (500 ul). The reaction mixture is stirred overnight at room temperature. The following morning, the crude reaction mixture is applied to a Sephadex G-25 column and eluted with water.

Fractions from the column are collected, protein containing fractions are pooled and lyophilized to give 56 mg of derivatized BSA. Titration of maleimide groups indicated incorporation of about nine maleimide groups per BSA.

(b) Synthesis of the Immunogen

A synthetic peptide (10 mg) (MW 3,300) corresponding to amino acids 38 through 71 of the beta subunit of thyroid stimulating hormone (TSH) is dissolved in a mixture of DMF (1.0 ml) and pH 6.6 phosphate buffer (1.0 ml; 0.1M phosphate). This material shows the presence of one sulfyhdryl group per peptide as determined by Ellman's reagent titration.

To the solution of β-TSH peptide was added modified BSA (1.5 mg) from Part (a). The solution was stirred overnight at room temperature in a capped vial. Purification of the crude reaction mixture by chromatography on a Sephadex G-25 column with water as eluent, followed by lyophilization of the recovered conjugate yields 18 mg of material which after analysis showed incorporation of four β-TSH peptides per BSA. (Formula 2; B=BSA; R=cyclohexylmethyl; X=6-aminocaproyl; n=1; Q=TSH subunit peptide; and r=4).

EXAMPLE 15

Synthesis of:

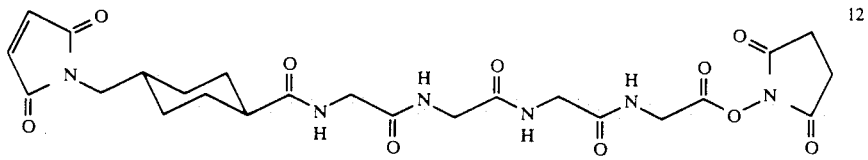

(a) Synthesis of Compound 7

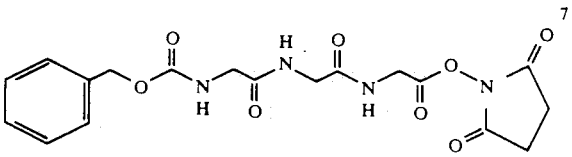

CBZ-triqlycine (4.0 g; Bachem Chem. Co.) is dissolved in 50.0 ml dry DMF. N-hydroxysuccinimide (1.42 g; 1.0 eq), and DCCI (2.55 g; 1.0 eq) are added, and the resulting mixture is stirred overnight at room temperature under a nitrogen atmosphere. The following morning, precipitated DCU is removed by filtration, and the resulting DMF solution is evaporated under reduced pressure to give a yellow oil. Recrystallization from ethyl acetate/chloroform gives the intermediate compound 7 (3.0 g) in 57% yield.

(b) Synthesis of Compound 8

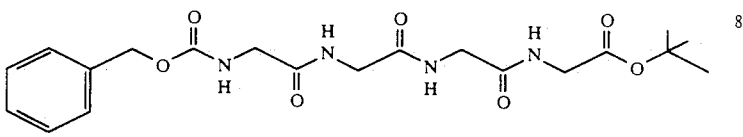

Glycine t-butyl ester hydrochloride (0.54 g; Sigma Chem. Co.) is suspended in dry DMF (25.0 ml). Compound 7 (1.35 g; 1.0 eq) from Part (a) is then added, along with triethylamine (1.62 g; 5.0 eq). The resulting solution is allowed to stir overnight at room temperature under nitrogen atmosphere. The following morning, solvent is removed under reduced pressure to give a crude product. Recrystallization from ethyl acetate/chloroform gives intermediate compound 8 (0.95 g) in 68% yield.

(c) Synthesis of Compound 9

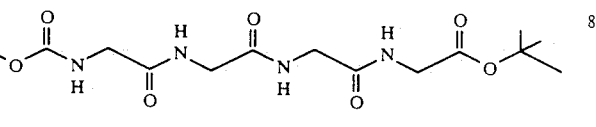

Compound 8 (0.95 g) from Part (b) is dissolved in dry methanol (300 ml). Glacial acetic acid (0.45 ml) is then added, and the solution is purged with nitrogen for 15 minutes. Palladium on carbon (1.5 g; palladium content 10%) is then carefully added, with stirring. A stream of hydrogen gas is bubbled through the stirring solution for three hours at room temperature. The solution is carefully purged with nitrogen for 15 minutes, then filtered. The filtrate solution is concentrated under reduced pressure to give intermediate compound 9 (700 mg) as the acetate salt.

(d) Synthesis of Compound 10

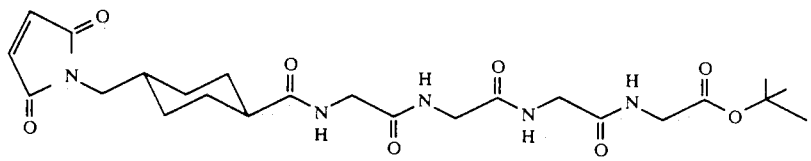

Compound 9 (700 mg; acetate salt) from Part (c) is dissolved in dry DMF (25 ml). N-(4-carboxycyclohexylmethyl) maleimide (697 mg) from Example 1 is then added, and the mixture is allowed to stir overnight at room temperature under nitrogen atmosphere. The following morning DMF is evaporated under reduced pressure to afford a crude product. Recrystallization from ethyl acetate/hexane affords intermediate compound 10 in 22% yield.

(e) Synthesis of Compound 11

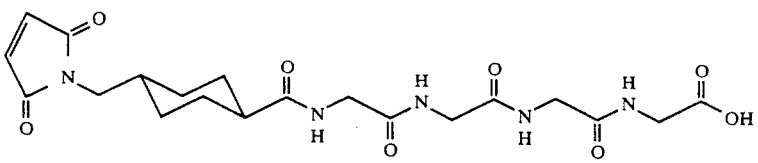

Compound 10 (225 mg) from Part (d) is suspended in chloroform (1.5 ml). Dry trifluoroacetic acid (1.5 ml) is then added, and the mixture is stirred at room temperature under a nitrogen atmosphere for a period of three hours. Solvent is evaporated under reduced atmosphere to give a crude product. Trituration with ethyl acetate gives intermediate compound 11 (127 mg) in 61% yield.

(f) Synthesis of Compound 12

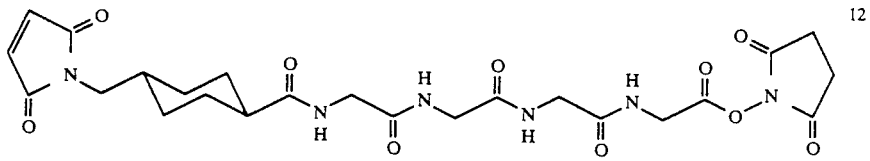

Compound 11 (100 mg) from Part (e) is dissolved in dry DMF (7.0 ml) along with N-hydroxysuccinimide (37.1 mg; 1.5 eq) and DCCI (221.5 mg; 5.0 eq). The reaction mixture is stirred overnight at room temperature under a nitrogen atmosphere. The following morning, precipitated DCU is removed by filtration, and DMF is evaporated under reduced pressure to give a crude solid. Trituration with chloroform gives compound 12 (86 mg) in 60% yield. (Formula 1; R=cyclohexylmethyl; n-4; X=glycine).

EXAMPLE 16

SYNTHESIS OF M-MALEIMIDOBENZOYLCAPROAMIDO-N-HYDROXY SUCCINIMIDE

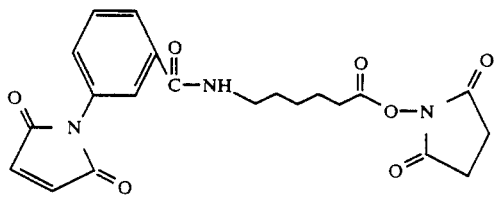

A round bottom flask equipped with a magnetic stirrer is charged with m-maleimidobenzoyl N-hydroxysuccinimide ester (0.314 g; 0.001 mole) obtained from Pierce Corporation dissolved in DMF (5.0 mL). 6-Aminocaproic acid (0.131 g; 1 equiv.) is added, and the resulting solution is stirred overnight at room temperature under nitrogen. After 18 hours, olicyclohexylcarbodiimide (DCCI; 0.206 g; 1.1 equiv.) is added followed by N-hydroxysuccinimide (0.115 g, 1 equiv.). The reaction solution is stirred for additional eight hours at room temperature under nitrogen. Precipitated dicyclohexylurea (DCU) is removed by filtration, and the resulting DMF solution is evaporated under reduced pressure. The resulting solid is purified by silica gel chromatography (5% methanol in chloroform) to give compound 13 in 50% yield. This compound is treated with aminocaproic acid in a manner identical to the method described in examples 2, 3 and 4 of this application to produce compounds of Formula I where n is up to ten, and R=phenyl).

The examples above are not intended to restrict the scope of this invention, which is defined in the claims which follow.

What is claimed is:

1. A conjugate for use in a diagnostic assay, comprising:

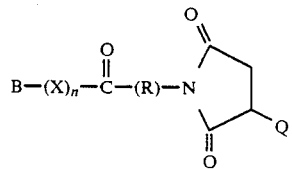

wherein B is an enzyme label, an antibody, or an antibody fragment;

Q is an antibody or an antibody fragment when B is an enzyme label, or an enzyme label when B is an antibod or antibody fragment;

X is an amino acid having from three to ten carbon atoms in a straight chain;

R is cycloalkyl or alkyl-cycloalkyl; and n is from three to ten.

2. The conjugate as recited in claim 1 wherein R is cyclohexylmethyl.

3. The conjugate of claim 1 wherein n is from three to five.

4. The conjugate of claim 3 wherein n is three.

5. The conjugate of claim 1 wherein X is a polyamide formed from repeated units of 6-aminocaproic acid.

6. The conjugate as recited in claim 1 wherein B is alkaline phosphatase or horseradish peroxidase.

7. The conjugate as recited in claim 1 wherein B is an antibody.

8. The conjugate as recited in claim 7 wherein B is goat-anti-rabbit IgG.

9. The conjugate as recited in claim 1 wherein Q is an antibody.

10. The conjugate as recited in claim 9 wherein Q is anti-AFP antibody, anti-CEA antibody, anti TSH antibody, or bovine gamma globulin.

11. The conjugate as recited in claim 1 wherein Q is an enzyme.

12. The conjugate as recited in claim 10 wherein Q is β-galactosidase, or alkaline phosphatase.

13. A conjugate for use in a diagnostic assay comprising:

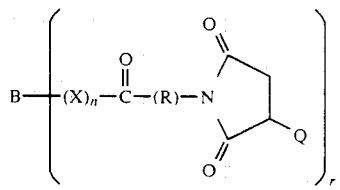

wherein X is a substituted or unsubstituted amino acid having from three to ten carbon atoms in a straight chain;
R is an alkyl, cycloalkyl, alkyl-cycloalkyl, or an aromatic carbocyclic ring;
n is from three to ten;
Q is an enzyme or antibody;
B is an enzyme when Q is an antibody, and B is an antibody when Q is an enzyme; and
r is from two to fifty.

14. The conjugate as recited in claim 13 wherein B is an enzyme.

15. The conjugate as recited in claim 14 wherein B is alkaline phosphatase.

16. The conjugate as recited in claim 15 wherein Q is anti-AFP IgG.

* * * * *